United States Patent
Dave et al.

(10) Patent No.: US 7,310,651 B2
(45) Date of Patent: Dec. 18, 2007

(54) MEDICAL MEDIA FILE MANAGEMENT SYSTEM AND METHOD

(76) Inventors: Ashok Dave, 3540 Woodcliff Rd., Sherman Oaks, CA (US) 91403; Andre Henderson, 18312 Benwood St., Covina, CA (US) 91722

( * ) Notice: Subject to any disclaimer, the term of this patent is extended or adjusted under 35 U.S.C. 154(b) by 617 days.

(21) Appl. No.: 10/921,637

(22) Filed: Aug. 18, 2004

(65) Prior Publication Data
US 2006/0058603 A1 Mar. 16, 2006

(51) Int. Cl.
G06F 7/00 (2006.01)
(52) U.S. Cl. ................................... 707/104.1
(58) Field of Classification Search ................ 707/104, 707/104.1, 512; 351/212, 247; 395/203; 345/356, 348, 302; 705/2, 3; 706/15, 45, 706/924; 600/300
See application file for complete search history.

(56) References Cited

U.S. PATENT DOCUMENTS

| | | | |
|---|---|---|---|
| 4,653,112 A | 3/1987 | Quimette | |
| 4,945,476 A | 7/1990 | Bodick et al. | |
| 4,958,283 A | 9/1990 | Tawara et al. | |
| 5,235,510 A | 8/1993 | Yamada et al. | |
| 5,241,472 A | 8/1993 | Gur et al. | |
| 5,272,625 A | 12/1993 | Nishihara et al. | |
| 5,581,460 A | 12/1996 | Kotake et al. | |
| 5,655,084 A | 8/1997 | Pinsky et al. | |
| 5,729,741 A | 3/1998 | Liaguno et al. | |
| 5,878,746 A | 3/1999 | Lemelson et al. | |
| 5,891,035 A * | 4/1999 | Wood et al. | 600/437 |
| 5,920,317 A * | 7/1999 | McDonald | 715/853 |
| 5,991,729 A | 11/1999 | Barry et al. | |
| 5,993,001 A | 11/1999 | Bursell et al. | |
| 6,031,526 A | 2/2000 | Shipp | |
| 6,275,869 B1 | 8/2001 | Sieffert et al. | |
| 6,463,417 B1 * | 10/2002 | Schoenberg | 705/2 |
| 6,687,685 B1 * | 2/2004 | Sadeghi et al. | 706/15 |
| 6,874,085 B1 * | 3/2005 | Koo et al. | 713/165 |
| 6,988,075 B1 * | 1/2006 | Hacker | 705/3 |
| 2002/0087503 A1 | 7/2002 | Judd et al. | |
| 2003/0035584 A1 | 2/2003 | Nicolas et al. | |

\* cited by examiner

*Primary Examiner*—Chong H Kim
(74) *Attorney, Agent, or Firm*—Stetina Brunda Garred & Brucker

(57) ABSTRACT

A medical communications and management system (MCMS) that is operative to compile, store, retrieve and transmit digitized medical information from a variety of medical imaging modalities, as well as digital information such as scanned in images, digital photographs, audio files, and digitized information corresponding to monitored physiological conditions, such as heart rate and the like. The MCMS is further operative to include personal patient identification information, such as retinal scans and fingerprints, and is capable of being archived to thus enable such digitized information to be readily accessed. To that end, it is contemplated that the MCMS of the present invention will be used in connection with an electronic medical record and facilitate compliance with HIPAA.

14 Claims, 1 Drawing Sheet

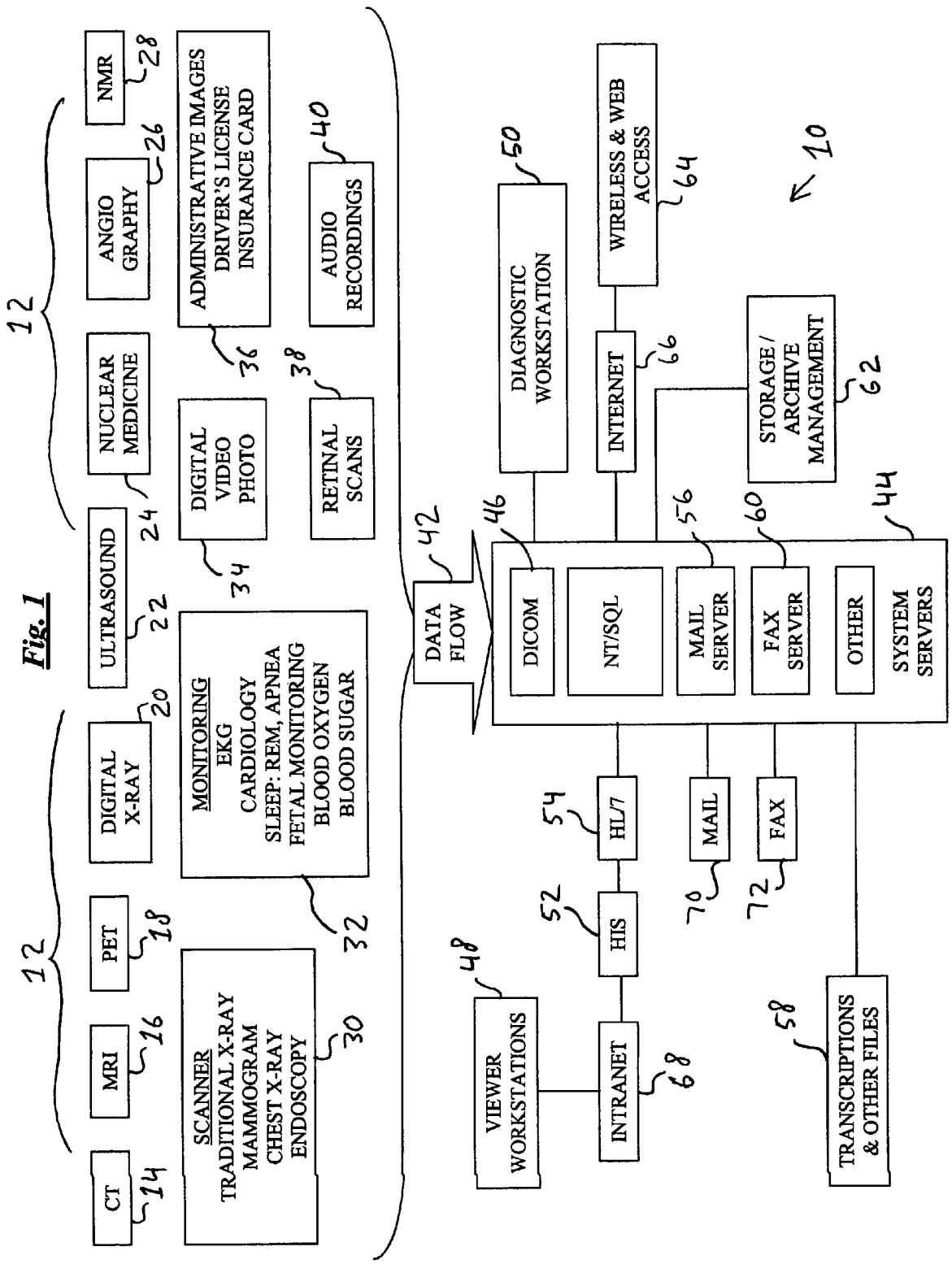

MEDICAL MEDIA FILE MANAGEMENT SYSTEM AND METHOD

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

This invention relates to a medical media file management system and method, and more particularly, to an improved system for generating, storing, retrieving and transmitting a plurality of medical data in a digital format, including but not limited to text, charts, still images, animation, graphics, video and audio, derivable from a variety of media image sources, such as computer data base files, hard copy print media, photographs, audio cassettes, video cameras, medical imaging equipment and medical monitoring equipment.

Medical imaging data, as derived from a variety of imaging modalities, is an essential component of health care and is often vital to properly assess a given patient's condition. In this regard, a number of complex imaging modalities are available which can generate digital images, including computerized tomography (CT), magnetic resonance imaging (MRI), positron emission tomography (PET), digital X-ray, ultrasound, nuclear medicine, angiography, and nuclear magnetic resonance (NMR). Other images can be converted into digital form through the use of a film digitizer or scanner for images obtained by more traditional X-ray radiography such as chest X-rays or mammograms, images taken through endoscopes, and physiological monitoring systems including wave patterns recorded in cardiology EKGs and in fetal monitoring. Each of these modalities complement one another depending on the type of diagnosis or monitoring being undertaken, so the systems are often used in conjunction with each other. However, each of these image acquisition devices typically operate as stand-alone devices with relatively small local storage capacity. Each modality is usually designed for the acquisition and subsequent analysis of a specific type of data and the images produced are optimized for a particular medical procedure. Consequently, each modality generates images with different levels of resolution and cannot communicate with another modality's data, resulting in inefficient storage and poor correlation of diagnostic data. These obstacles can prevent the timely and accurate diagnosis of disease. Although it is typically possible to "export" the images from a proprietary radiology (imaging) modality workstation to an industry-standard format such as "Digital Imaging Communications in Medicine" (DICOM) 3.0, several limitations remain as discussed subsequently. In practice, viewing of radiology medical images typically requires a different proprietary "workstation" for each manufacturer and the manufacturer specific Picture Archival and Communications System (PACS) typically extends its use only for the viewing and diagnosis of the radiology-specific images. Even more archaic, and perhaps the more conventional practice is to bundle the various types of imaging data, such as developed X-ray films, ultrasound photographs, and the like, with the actual physical patient file.

Similarly, from a monitoring standpoint, breathing rate, heart rate, and blood-oxygen levels are also essential and can be recorded on an ongoing basis using patient monitoring equipment. Furthermore, monitoring data are generated during EKG tests, treadmill endurance tests, fetal monitoring during labor, sleep research on REM cycles or sleep apnea, and blood sugar level information from diabetes tests. Despite the ability to generate and store such information digitally, in standard practice much of the data is recorded on long strips of paper, which uses significant resources and becomes difficult and bulky to store in the patient files in paper form.

In addition to medical imaging and monitoring data that must be generated and stored, substantial patient data must also typically be collected and retained. Currently, during most hospital check in procedures, a patient may need to fill out numerous forms providing proof of identity and of insurance, as well as forms relating to medical history. While many medical facilities are moving toward computer records of the textual information, there is no efficient way to keep copies of photographs and other media files containing images pertinent to the patient file without actually pulling the paper file from the records office, which can be at a remote location. When a doctor or nurse conducts an interview of the patient, the notes are placed in the file. Although it is not current typical practice, an audio recording of the interview may be useful if there was a simple and efficient means for storing the audio information rather than dealing with loose bulky tapes in the patient file that could inadvertently become erased.

Further problematic is when the patient's primary physician orders tests to monitor the patient's physiological results, which in turn causes the admissions process to be repeated at the monitoring facility. Depending on the duration of the monitoring tests, limited sections of the patient's monitoring response are printed out and marked to highlight areas requiring attention and are folded into a file for the doctor to view at a later time. In cases with sleep studies or recovery from surgery, monitoring may be conducted for several hours or days.

If the patient's primary physician orders an imaging-based test to diagnose or assess disease, the admissions process is likewise repeated at the imaging facility. Typically days after the imaging procedure, the patient's primary physician receives a written report generated by a specialist physician who has interpreted the images but who is unlikely to understand the patient's clinical history and is unaware of any other test results. The patient's primary physician typically does not view the images directly but rather makes a treatment decision based entirely on written reports generated by one or more specialist physicians. The current process raises several limitations on efficient diagnosis and treatment of patients. The primary physician does not see the images unless they are printed to film or the doctor travels to another department and makes a request. Each proprietary modality workstation at a separate location requires training in how to use the software to view the images, and images from the same patient but different modalities cannot be viewed side-by-side, even using proprietary workstations. The primary physician cannot show the patient his/her images in the physician's office while explaining the diagnosis; and the patient cannot transport his/her images to another physician's office for a second opinion.

As if such practices were not already burdensome, recently implemented legislation has made the ability for hospitals and physicians to generate and assess patient information, and in particular, medical imaging data even more difficult. Specifically, The Health Insurance Portability and Accountability Act (HIPAA) of 1996, signed into law on Aug. 21, 1996, sets forth numerous regulations related to the practice of medicine, particularly with respect to the handling of healthcare-related information, that are intended to reduce the administrative costs of healthcare. Essentially, HIPAA sets forth provisions related to the development and implementation of standardized electronic transactions and the implementation of privacy and security procedures to insure confidentiality and prevent the misuse of patient information. With respect to the former, namely, standardized transactions, the same are to be used no later than Oct. 16, 2003.

Among the many requirements set forth in HIPAA is that any medical practice that electronically sends or receives certain transactions must send and receive them in a standard format. Such transactions expressly include claims, remittance and payment advice, claims status, enrollment and dis-enrollment in a health plan, premium payments, eligibility inquiries and responses, referral certifications and authorization, coordination of benefits, first reports of injury, and claims attachments. In this regard, it is contemplated that a medical practice will be able to submit a claim for a patient, irrespective of the payor involved (e.g., insurance company, health maintenance organization, etc.). As a result, it is contemplated that all transactions will be standardized in nature, which will include the uniform use of codes typically associated with conventional billing practices, such as diagnosis codes (i.e., ICD-9-CM), procedure/service codes (CPT-4), drug codes (NDC), and other service codes (HCPCS), among others.

With respect to imaging data, however, particularly when generated and stored in physical patient files and not otherwise kept in a format that can facilitate the electronic transmission of data, is operative to defeat the entire legislative purpose behind HIPAA. Furthermore, it is practically impossible and cost-prohibitive to duplicate Radiology Film Storage when the Films are not in a Digital Format, thus making the task of HIPAA required back-ups and disaster recovery meaningless. Accordingly, there is a substantial need in the art for a medical media file management system and method that is operative to not only facilitate the collection, storage, retrieval and transmission of medical imaging data capable of being generated from a wide variety of imaging modalities, but further is operative to facilitate the collection, storage, retrieval and transmission of other types of patient data, such as digital photographs, scanned in images of patient identification and insurance information, and recorded audio (e.g., transcription) files, to thus enable all such information to be retained in an efficient digital format. There is further a need for such a system and method that can be readily integrated with virtually all types of medical imaging modalities, as well as conventional devices, such as digital cameras, that can enable all information derived thereby to be stored and retained in a digitized format. There is still likewise a need in the art for such a system and method that can be incorporated as part of an existing electronic medical record (EMR) which can thus greatly reduce the amount of physical storage associated with storing personal files, as well as facilitate the handling and exchange of patient information and transactions related thereto, especially in compliance with HIPAA. There is still further a need in the art for such a system and method that can be constructed utilizing existing technology, is of low cost, is exceptionally efficient and can be integrated into virtually all types of existing medical and hospital practices and procedures.

BRIEF SUMMARY OF THE INVENTION

The present invention specifically addresses and alleviates the above-identified deficiencies in the art. In this regard, the present invention is directed to a Media Communications and Management System (MCMS) that is operative to serve as the basis of an enterprise-wide image, document, recording and file management facility for any healthcare provider. Various imaging modalities can be directly captured and linked to the patient record in the Hospital Information System (HIS) utilizing the industry standard HL/7 protocols. The imaging modalities may include CT, MR, Ultrasound, and radiography images and movies, and may also include other patient specific documentation such as photographs of the patient or copies of the patient's drivers license, Social Security Card, and insurance card. Additional media may also be stored including sound files from cardiac and fetal ultrasounds, voice recordings, and retinal scans.

The MCMS can be manipulated by a Mini-PACS Diagnostic Workstation and/or any Network attached Windows Workstation as a medical viewer workstation. The system may be used to convert medical information from a plurality of media formats in to an integrated format. The invention also relates to methods to manipulate digital medical media in such a way that multiple media modalities from multiple different vendors can be assembled into a single database without loss of diagnostic information. The MCMS can integrate non-conventional image/digital data, such as digital photographs and audio files, as part of a patient's digitized medical information, as well as data such as retinal scans and fingerprints, to thus enable a patient's medical information to be comprehensively collected, stored, retrieved and transferred.

FIGURE DESCRIPTION

These as well as other features of the present invention will become more apparent upon reference to the drawings.

FIG. 1 diagrammatically illustrates the overall architecture of an embodiment of the Media Communications and Management System.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present invention resides in an interface of medical media data storage, retrieval and communication components with the integration of media image and audio manipulation control mechanisms that enable a user of the system to both efficiently store multiple types of information from diverse media, and to rapidly access, copy, transmit and/or store any such stored media image for analysis. The structure, control and arrangement of these components and control mechanisms have been illustrated in the drawings that illustrate the systems and methods of the present invention.

Referring now to FIG. 1, there is shown an overall flow diagram of the Media Communications and Management System (MCMS) 10. The key input technology components of MCMS 10 include various media modalities 12, including but not limited to computerized tomography (CT) 14, magnetic resonance imaging (MRI) 16, positron emission tomography (PET) 18, digital X-ray 20, ultrasound 22, nuclear medicine 24, angiography 26, and nuclear magnetic resonance (NMR) 28. Other non-digital images 30 can be converted into digital form through the use of a film digitizer or scanner 30. These images may include more traditional X-ray radiography such as chest X-rays or mammograms, or images taken through endoscopes. The output from physiological monitoring systems 32 such as wave patterns recorded in cardiology EKGs, sleep clinic REM or sleep apnea measurements, or in fetal monitoring can also be captured by the system. Images, movies, and sound may be recorded from any device 34, including but not limited to digital cameras, camcorders, camera cell phones, and the like. Photocopies or scanned images 36 of drivers licenses, social security cards, and other identification, as well as virtually any document can also be digitized through the scanner. Retinal scans 38, fingerprint data, and audio recordings 40 also provide input to the MCMS.

The data flow from the various Radiology (Imaging) input components is directed via a communications link 43 to one or more system servers 44 having one or more databases associated therewith, including a Digital Imaging Communications in Medicine (DICOM) format caching server 46, a mail server 56, a fax server 60, all of which are linked to one or more information retrieval devices, such as a diagnostic workstation with mini-Picture Archiving and Communication System (mini-PACS) 50, a viewer workstation 48 connected through an Intranet connection 68 to a Hospital Information System (HIS) server 52 via HL/7 standards 54, a set of user files including office files and transcriptions 58, a store/archive management system 62, an Intranet/Internet connections 66, 68 to facilitate Web-based access. Conventional mail 70 and fax 72 capabilities are also integrated as part of the information distribution capabilities of the present invention.

The storage/archive management system 62, which stores and readily retrieves media files, is linked to a Storage System, which in turn is linked to an archive to facilitate back-ups and disaster recovery. It is likewise contemplated that such media files can be accessed by a personal computer or content requesting server via wireless and/or web access 64 through an Internet communications link 66.

In a preferred embodiment, the radiology imaging modalities have the DICOM format capability and are linked with an Intel based Server with either an attached or peripheral file storage capability. The MCMS software may consist of various applications and systems including DICOM Server, DICOM Viewer, Windows SQL 2000, Windows 2000 Server, and Storage Management. The network communications can follow a TCP/IP Network and DICOM 3.0 protocol. Optional interfaces include HL/7 to HIS/RIS and HL/7 to the various modality software systems.

The integration process uses modalities that are configured to capture consistent patient examination data. The modalities are configured to auto-send patient index and image files over the TCP/IP network to the Windows 2000/ DICOM Server. The images are stored as individual files located on the file storage on the DICOM Server along with a Patient Record Index. The Patient Record Index will preferably consist of the following Data Elements: Physician Name, Patient Identification, Patient Name, date of birth, sex, examination type, image number, image date, modality, modality manufacturer, modality model, and the like. Images are accessed by any workstation with DICOM-based viewing software using any of the Patient Record Index data elements. In addition, for diagnostic viewing, images can be accessed from a Radiology Diagnostic work station with any third party diagnostic software. Image file management is controlled through storage management software based rules, which can be programmed to archive based on data elements, such as date of exam, calendar days or file size to optimize the cost of the overall storage media. The same architecture also forms the foundation for capture of other media including scanned documents. All the file elements are attached to the core patient management system to form the electronic information folder for the patient information.

In use, the MCMS 10 will be operative to provide a comprehensive database of digitally stored information that greatly facilitates the ability of medical information to be compiled, stored, retrieved and transferred. It is contemplated that through such system, a digital patient file can be created that can enable all pertinent information related to a patient that has not heretofore been capable of being digitized, and much less digitized from a variety of image modalities, to be compiled in a single retrievable file. For example, it is contemplated that a patient entering a hospital implementing the MCMS will be able to provide identification information and proof of insurance, such as through drivers licenses, Social Security card, insurance cards, and the like that can be scanned in, along with any other pertinent patient information. The MCMS will further be operative to allow further input of information during a patient examination, such as digital photographs, recorded patient interviews, recorded statements by the treating physician or other hospital staff, or any other information that may be pertinent to the treatment of a given patient, such as medical histories provided by relatives and/or in the case of accidents, statements from witnesses or law enforcement officials. Along these lines, it is contemplated that other data specific to the patient, such as finger prints and a generation of a retinal scan can be included within the patient's file to thus serve as a basis of identifying a particular individual. In this regard, such uniquely identifying features may be included as part of a database that can enable the medical records generated through the MCMS of the present invention to be readily accessed and forwarded to a hospital, physician or any other type of medical facility to thus provide a readily retrievable medical history for that specific individual.

In addition to the digitized information above, it is further contemplated that any and all imaging data as referenced herein may further be included as part of the patient's diagnosis. As discussed above, imaging modalities such as X-rays, ultrasound and the like can be digitized and stored within a patient's specific file. Advantageously, such process thus eliminates the need to store such image data, such as X-ray films and the like, that are known in the art to be costly, space inefficient and exceptionally difficult to archive and access. Moreover, by virtue of having the capability to store image data in a digitized format, the MCMS of the present invention is operative to uniformly store and make accessible image data irrespective of the type of image data that is warranted, whether CT, MRI, PET, EKG or Scanned Images, for example.

Due to the simplicity by which the compiled digitized information is compiled through the MCMS of the present invention, it is contemplated that the MCMS may either be operative to exist as either a stand alone electronic record (EMR) system or otherwise be incorporated as part of a conventional EMR system with HL/7-based interfaces to the HIS 52.

As is well-known in the art, a variety of commercial software products are available for generating electronic medical records, as well as facilitating electronic claims filing and other medical management tasks that, in addition to increasing the efficiency of conventional health care practices, further help ensure compliance with HIPAA regulations by enhancing the security associated with patient information and utilizing all applicable standard formats necessary to conduct and codify electronic transmissions. By complementing such systems with the ability to capture not only medical imaging data but other pertinent patient information, the MCMS of the present invention is operative to greatly enhance the capability of such conventional EMR systems to not only provide greater efficiency but also comply with HIPAA.

In a related application, it is contemplated that the MCMS will further be operative to facilitate the ability to create archives of patient histories that, as discussed above, can be readily accessed as necessary. To that end, it is contemplated that the MCMS of the present invention will be operative to create redundancy of patient information such that a patient's specific medical record can be stored in multiple archives and thus not be limited to a single patient file that can be subjected to damage or misplacement. In this respect, it is contemplated that once a sufficiently large database of patient files has been created, the same can be accessed as may be necessary in the event of natural disasters, acts of war or terrorism and the like to thus enable medical records for one or more patients to be readily accessed at a treating facility by simply accessing such information via the Internet. Accordingly, it should be understood that the MCMS of the present invention has wide spread application for use in not only facilitating the ability to generate, to store, retrieve and transmit medical information in a digital format, but as well as facilitate the ability of health care providers to have continuous access to patient information that is constantly kept up to date and is capable of being identified with a specific individual. Moreover, because of the digitized format by which the information is retained via the MCMS of the present invention, such information can be readily communicated via conventional communication lines, and especially the Internet, which thus provides an extremely efficient manner that such information can be readily accessed.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed:

1. A medical communications and management system for facilitating the generation, storage, retrieval and transmission of digitized medical information comprising:
   a) at least one server system having a database associated therewith, said server system and database associated therewith being operative to receive, store, retrieve and transmit medical image data generated by a medical image modality selected from the group consisting of computerized tomography, magnetic resonance imaging, positron emission tomography, digital x-ray, ultrasound, nuclear medicine, angiography and nuclear magnetic resonance, said server system and database associated therewith further being operative to receive, store, retrieve and transmit digital data corresponding to an item of digitized information selected from the group consisting of an audio file, a scanned image and a digital photograph, said server system and database associated therewith having a single retrievable file for receiving, storing, and retrieving computerized tomography, magnetic resonance imaging, positron emission tomography, digital x-ray, ultrasound, nuclear medicine, angiography, nuclear magnetic resonance, scanned images, digital photographs, and digital audio;
   b) a communications link; and
   c) at least one information retrieval device operatively coupled by said communications link to said server system and database associated therewith, said information retrieval device being selected from the group consisting of a hospital information system, an e-mail server, a fax server, and an archive server.

2. The medical communications and management system of claim 1 wherein the medical communications and management system is integrated within an electronic medical records system.

3. The system of claim 1 wherein said server system and database associated therewith are further operative to transmit said digitized information in response to requests made by said information retrieval device.

4. The system of claim 3 wherein said information retrieval device further comprises a server or personal computer.

5. The system of claim 1 further comprising at least one medical imaging modality operatively coupled via a communications link to said server system with database associated therewith.

6. The system of claim 5 wherein said imaging modality comprises a device operative to generate digital images selected from the group consisting of computerized tomography, magnetic resonance imaging, positron emission tomography, digital x-ray, ultrasound, angiography and nuclear magnetic resonance.

7. The system of claim 5 wherein said server system and database associated therewith are further operative to receive, store, retrieve and transmit digital information corresponding to a monitored physiological condition of a patient.

8. The system of claim 7 wherein said monitored physiological condition is selected from the group consisting of breathing rate, heart rate, blood-oxygen levels and sleep patterns.

9. A method for generating, storing, retrieving and transmitting digitized medical information comprising the steps:
   a) generating medical image data from a medical image modality selected from the group consisting of computerized tomography, magnetic resonance imaging, positron emission tomography, digital x-ray, ultrasound, angiography and nuclear magnetic resonance;
   b) generating digitized information corresponding to a digitized audio file, scanned in image and digital photograph;
   c) transmitting said digitized data in steps a) and b) to a server system having a dedicated database associated therewith, said server system and database associated therewith being operative to store, retrieve and transmit such digitized data in a single retrievable file;
   d) providing a communications link between said server system and database associated therewith in step e) with an information retrieval device; and e) requesting information from said information retrieval device through said communications link to said server system with database associated therewith, said server system and database associated therewith being operative to retrieve and transmit said digitized data received in steps a) and b) in response to said request made by said information retrieval device.

10. The method of claim 9 wherein step e), said information retrieval device comprises a hospital information system server, personal computer, a viewer workstation, and a diagnostic workstation.

11. The method of claim 9 wherein said communications link provided in step d) comprises an Internet connection.

12. The method of claim 9 wherein said communications link provided in step d) comprises an Intranet connection.

13. The system of claim 1 wherein said server system having said database associated therewith is further operative to receive, store, retrieve and transmit digital data corresponding to an item of digitized information selected from the group consisting of a scanned image of a fingerprint and a retinal scan.

14. The method of claim 9 wherein step b) further comprises the step generating digitized information corresponding to an individual's fingerprints or an individual's retinal scan.

* * * * *